(12) United States Patent
Witkowski

(10) Patent No.: US 11,268,945 B2
(45) Date of Patent: *Mar. 8, 2022

(54) METHOD FOR QUANTITATING RETAIL PAPER TOWEL LINT

(71) Applicant: GPCP IP Holdings LLC, Atlanta, GA (US)

(72) Inventor: Terry P. Witkowski, Neenah, WI (US)

(73) Assignee: GPCP IP Holdings LLC, Atlanta, GA (US)

(*) Notice: Subject to any disclaimer, the term of this patent is extended or adjusted under 35 U.S.C. 154(b) by 0 days.

This patent is subject to a terminal disclaimer.

(21) Appl. No.: 17/111,082

(22) Filed: Dec. 3, 2020

(65) Prior Publication Data
US 2021/0088501 A1   Mar. 25, 2021

Related U.S. Application Data

(62) Division of application No. 16/890,261, filed on Jun. 2, 2020, now Pat. No. 10,900,948, which is a division of application No. 15/946,313, filed on Apr. 5, 2018, now Pat. No. 10,725,016.

(60) Provisional application No. 62/527,677, filed on Jun. 30, 2017.

(51) Int. Cl.
G01N 33/34 (2006.01)
G01N 1/28 (2006.01)
D21H 27/00 (2006.01)

(52) U.S. Cl.
CPC ......... G01N 33/346 (2013.01); G01N 1/2813 (2013.01); D21H 27/002 (2013.01); D21H 27/004 (2013.01)

(58) Field of Classification Search
CPC .................. G01N 1/2813; G01N 33/346
See application file for complete search history.

(56) References Cited

U.S. PATENT DOCUMENTS

| | | |
|---|---|---|
| 3,563,241 A | 2/1971 | Evans |
| 4,287,251 A | 9/1981 | King |
| 4,347,749 A | 9/1982 | Heintze |
| 5,885,363 A | 3/1999 | Nakamura |
| 6,230,548 B1 | 5/2001 | Han |
| 7,037,394 B2 | 5/2006 | Christensen |
| 7,597,012 B2 | 10/2009 | Yao |
| 8,146,447 B2 | 4/2012 | Lee |
| 8,540,846 B2 | 9/2013 | Miller |
| 2002/0056317 A1 | 5/2002 | Strandqvist |
| 2008/0028873 A1 | 2/2008 | Yao |
| 2009/0044643 A1 | 2/2009 | Gipp |
| 2009/0056891 A1 | 3/2009 | Wiwi |
| 2012/0177888 A1 | 7/2012 | Escafere |
| 2013/0340541 A1 | 12/2013 | Qin et al. |

Primary Examiner — Benjamin R Schmitt
(74) Attorney, Agent, or Firm — Laura L. Bozek

(57) ABSTRACT

A method for quantitating the amount of lint shed from a paper towel, the method comprising: preparing a sample of paper towel to be analyzed; depositing lint from the sample onto a substantially lint-free surface by moving the sample thereupon in a specific pattern; collecting the lint deposited on the surface, wherein collecting the lint deposited on the surface comprises, substantially immediately upon depositing lint from the sample onto the surface, washing the deposited lint from the surface into a tared, cleaned, empty vessel; and determining the amount of collected lint.

21 Claims, 7 Drawing Sheets

METHOD FOR QUANTITATING RETAIL PAPER TOWEL LINT

CROSS-REFERENCE TO RELATED APPLICATIONS

The present application is a divisional of and claims priority under 35 U.S.C. § 119(e) to U.S. patent application Ser. No. 16/890,261 filed on Jun. 2, 2020, published as U.S. Patent Application Publication No. US 2020/0292520 A1, which is a divisional of and claims priority to U.S. patent application Ser. No. 15/946,313 filed on Apr. 5, 2018, now U.S. Pat. No. 10,725,016 B2, which is a non-provisional application claiming priority to U.S. Provisional Patent Application No. 62/527,677 filed on Jun. 30, 2017, and all entitled "Method for Quantitating Retail Paper Towel Lint," the disclosure of each of which is hereby incorporated by reference in its entirety.

STATEMENT REGARDING FEDERALLY SPONSORED RESEARCH OR DEVELOPMENT

Not applicable.

REFERENCE TO A MICROFICHE APPENDIX

Not applicable.

BACKGROUND

Technical Field

The present disclosure relates to linting of paper towels; more specifically, this disclosure relates to a method of quantitating paper towel lint; still more specifically, this disclosure relates to a method of quantitating paper towel lint that utilizes a specific wiping pattern to maximize lint deposition, a pre- and/or inter-test cleaning procedure, and/ or a specific rinse water sprayer.

Background

Pulp fibers, such as softwood fibers and hardwood fibers, are incorporated into numerous nonwoven materials. Such nonwoven materials are utilized in a variety of applications. For example, pulp fibers are used to form tissue products, including facial tissues, bath tissues, paper towels, industrial wipers, and the like. Pulp fibers are relatively inexpensive to obtain, which enables the production of relatively inexpensive products that may be disposed of after a single use.

Wiping products incorporating pulp fibers, such as paper towels, facial tissues, bath tissues and other similar products are designed to include several important properties. For example, the products are typically designed to have good bulk and a soft feel, and to be highly absorbent, while also exhibiting sufficient strength for the intended application, and tear resistance, even while wet. Unfortunately, when steps are taken to increase one desired property of the product, other characteristics of the material can be adversely affected. For example, in the manufacture of paper products, such as facial tissue, bath tissue, paper towels, dinner napkins and the like, a plethora of product properties can be imparted to the final product through the use of chemical additives applied in the wet end of the tissue making process. Two of the attributes imparted to tissue through the use of wet end chemical additives are strength and softness. Specifically for softness, a chemical debonding agent is normally utilized. Via disruption of fiber-to-fiber bonds, incorporation of such debonding agents increases the softness of the tissue sheet.

Debonding tends to increase levels of lint and slough in the product. Lint and slough can generally be defined as the tendency of the fibers in the paper sheet to be rubbed from the sheet when handled. Indeed, while softness increases, such increase is obtained at the expense of an increase in lint and slough in the product relative to an untreated control. For example, in a blended (non-layered) tissue sheet, the level of lint and slough is typically inversely proportional to the tensile strength of the tissue sheet.

As efforts to reduce slough and lint without a noticeable loss of bulk and softness have not been entirely successful, many disposable wiping products, such as paper towels and facial tissues, have an undesirable tendency to generate lint on surfaces after use. Such a tendency, which may be more noticeable, for example, when wiping a mirror or a black surface, may be viewed by a consumer or other user as undesirable or even unacceptable.

In view of the above, a need exists for a method of quantitating the amount of lint shed from a product, such as a paper towel, during a wiping motion. Such a method may be useful in producing wiping products having a reduced tendency to lint when used in a wiping motion.

SUMMARY

Disclosed herein is a method for quantitating the amount of lint shed from a paper towel, the method comprising: preparing a sample of paper towel to be analyzed; depositing lint from the sample onto a surface, which has been cleaned, by moving the sample thereupon in a specific pattern comprising a plurality of directional changes; collecting the lint deposited on the surface; and determining the amount of collected lint.

Also disclosed herein is a method for determining the amount of lint shed from a paper towel, the method comprising: preparing a sample of paper towel to be analyzed; depositing lint from the sample onto a substantially lint-free surface by moving the sample thereupon in a specific pattern; collecting the lint deposited on the surface; measuring the number, the average length, and the average width of the fibers in the collected lint; and calculating the amount of collected lint as the total fiber area ($mm^2$), by multiplying the average fiber length (mm) by the average fiber width (mm) and the fiber count and subtracting a blank therefrom, wherein the blank is calculated as the amount of lint collected from the substantially lint-free surface in the absence of the depositing step.

Further disclosed herein is a method for quantitating the amount of lint shed from a paper towel, the method comprising: cleaning a rectangular deposition surface having a short dimension and a long dimension, wherein cleaning comprises spraying the entire surface with glass cleaner, using a substantially lint-free squeegee to push the glass cleaner off one of two short sides of the surface, and using a substantially lint-free sponge to wipe the edges of the surface substantially free of lint; preparing a sample of paper towel to be analyzed; depositing lint from the sample onto the cleaned surface by moving the sample thereupon in a specific pattern; collecting the lint deposited on the surface; and determining the amount of collected lint.

Also disclosed herein is a method for quantitating the amount of lint shed from a paper towel, the method comprising: preparing a sample of paper towel to be analyzed; depositing lint from the sample onto a substantially lint-free surface by moving the sample thereupon in a specific pattern; collecting the lint deposited on the surface, wherein collecting the lint deposited on the surface comprises, substantially immediately upon depositing lint from the sample onto the surface, washing the deposited lint from the surface into a tared, cleaned, empty vessel; and determining the amount of collected lint.

Further disclosed herein is a method for quantitating the amount of lint shed from a paper towel, the method comprising: preparing a sample of paper towel to be analyzed, wherein preparing the sample comprises wrapping the sample around a solid support, to provide a wrapped support; depositing lint from the sample onto a surface, which has been cleaned, by moving the sample thereupon in a specific pattern comprising a plurality of directional changes; collecting the lint deposited on the surface; and determining the amount of collected lint, wherein the surface is substantially rectangular, having a long dimension and a short dimension, wherein the solid support is substantially rectangular, having a long dimension and a short dimension, and wherein wrapping the sample around the solid support further comprises placing the solid support on the sample on a side of the sample opposite a side of the sample to contact the surface during lint deposition and wrapping the sample around the solid support, with a machine direction of the sample parallel to the short dimension of the solid support.

Also disclosed herein is a method for quantitating the amount of lint shed from a paper towel, the method comprising: preparing a sample of paper towel to be analyzed, wherein preparing the sample comprises wrapping the sample around a solid support, to provide a wrapped support, wherein wrapping the sample around the solid support further comprises placing the solid support on the sample on a side of the sample opposite a side of the sample to contact the surface during lint deposition and wrapping the sample around the solid support; depositing lint from the sample onto a surface, which has been cleaned, by moving the sample thereupon in a specific pattern comprising a plurality of directional changes; collecting the lint deposited on the surface; and determining the amount of collected lint.

BRIEF DESCRIPTION OF THE DRAWINGS

For a more complete understanding of the present disclosure and the advantages thereof, reference is now made to the following brief description, taken in connection with the accompanying drawings and detailed description, wherein like reference numerals represent like parts.

FIG. 5 is a schematic of a deposition surface cleaning setup during a squeegee stage according to an embodiment of this disclosure;

FIG. 6 is a schematic of a deposition surface cleaning setup during a sponge wipe stage according to an embodiment of this disclosure;

DETAILED DESCRIPTION

Figure 1:
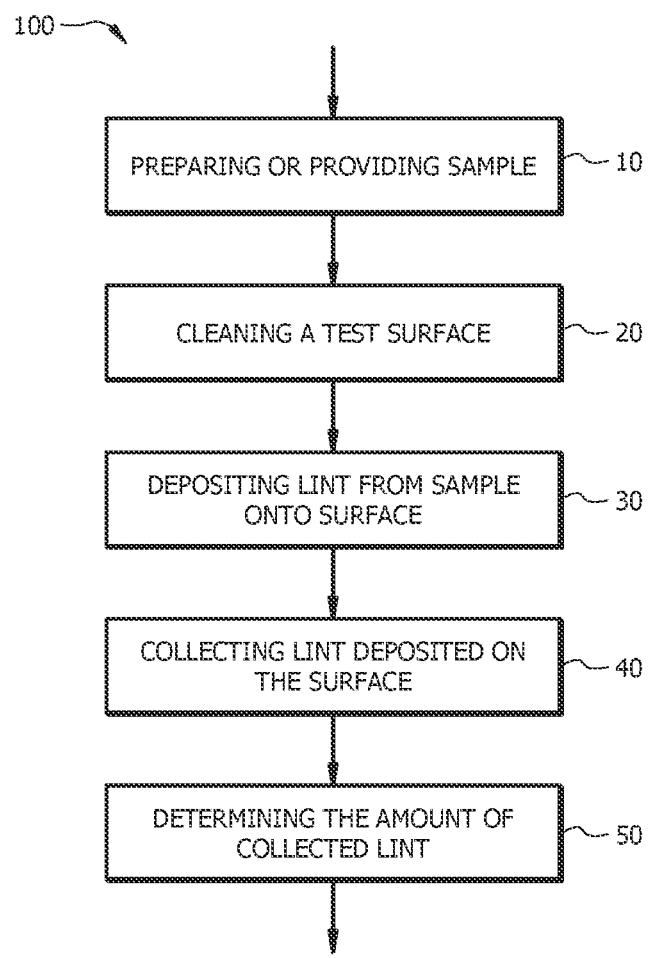
FIG. 1 is a flow diagram of a method for quantitating paper towel lint according to an embodiment of this disclosure.

Herein disclosed is a method for quantitating paper towel lint. The method can be utilized to determine the amount of lint shed from a paper towel during a wiping motion. 'Lint' as used herein means any material that originated from a fibrous structure, such as, without limitation, a paper towel or tissue product comprising the fibrous structure, that remains on a surface after the fibrous structure or product formed therefrom has come into contact therewith. The amount of lint, calculated as described hereinbelow as the total area of fiber deposited on a surface during testing, indicates the tendency of the fibers in the fibrous structure to be rubbed therefrom when utilized.

Although described hereinbelow with reference to a paper towel, a fibrous structure tested via the herein-disclosed method may be another wiping product. In general, the lint deposited during a wiping motion by any wiping product containing pulp fibers may be assessed according to the method of this disclosure. Such wiping product may comprise, for example, a paper towel, an industrial wiper, a premoistened wiper, or the like, including other nonwoven, woven or knitted wiping products. In embodiments, the wiping product comprises a tissue web, such as a paper towel, industrial wiper, and the like. Such tissue web may, for example, have a basis weight of from about 10 gsm to about 150 gsm. Bath tissues and facial tissues, for example, typically have a basis weight of from about 10 gsm to about 35 gsm, while paper towels and other wiping products may have a basis weight of from about 40 gsm to about 80 gsm.

The wiping product may be a retail or non-retail product, e.g., a retail consumer paper towel or a non-retail paper towel. The fibrous product may contain one ply or may contain multiple plies. Furthermore, although primarily described, and shown in the drawings, as being carried out manually (i.e., via human), it is to be understood that quantitating lint according to the method of this disclosure can be mechanized or automated.

The method according to this disclosure will now be described with reference to FIG. 1, which is a flow diagram of a method 100 for quantitating paper towel lint according to an embodiment of this disclosure. Method 100 comprises preparing or providing a sample to be analyzed at 10, depositing lint from the sample onto a surface 30, collecting lint deposited on the surface at 40, and determining the amount of collected lint at 50. The method can further comprise cleaning the test or deposition surface at 20, prior to depositing lint from a sample onto the surface at 30. Each of the steps of the method will be described in more detail hereinbelow.

As indicated in FIG. 1, a method according to this disclosure comprises preparing or providing a sample to be analyzed 10. As noted above, the sample may comprise a paper towel, and will be described herein as such. However, in embodiments, the sample may be another fibrous, lint-producing material, such as, without limitation, bath tissue, facial tissue, and the like. The sample may be preconditioned or conditioned prior to analysis. For example, in embodiments, the sample, or a roll from which the sample is taken, is allowed to acclimate for a time in a controlled environment prior to testing. The sample may be conditioned in a standard conditioning and testing atmosphere, according to TAPPI TM-402, wherein the controlled environment comprises a temperature of 72° and a relative humidity of 50%. The time for acclimation may be greater than 2 hours.

A sample may be cut from a roll of paper towel which has been conditioned as noted above. A sample of a desired size is cut from the roll. In order to minimize/prevent foreign lint from contaminating the sample, cutting of the sample is effected just prior to lint testing, and is not performed well in advance of testing. For example, the sample(s) may be cut within 3, 4, or 5 minutes of lint deposition via step 30, in embodiments.

Figure 2A:
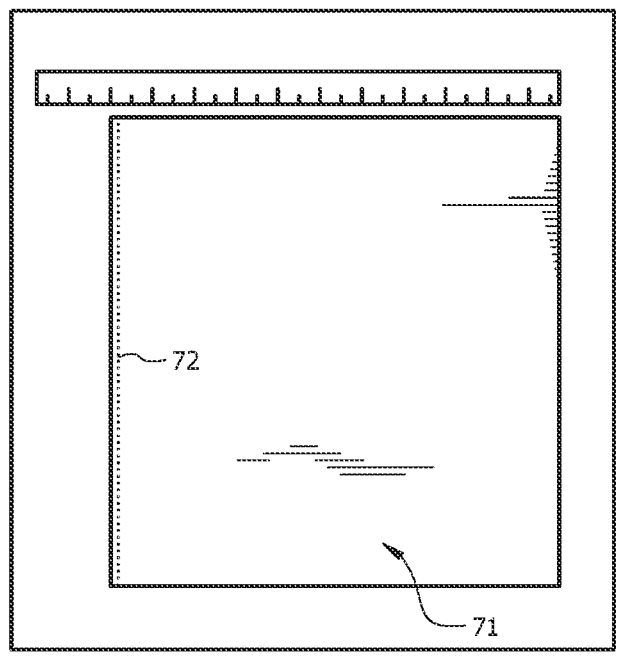
FIG. 2A is a depiction of a suitable full sheet paper towel test sample according to an embodiment of this disclosure.
Figure 2B:
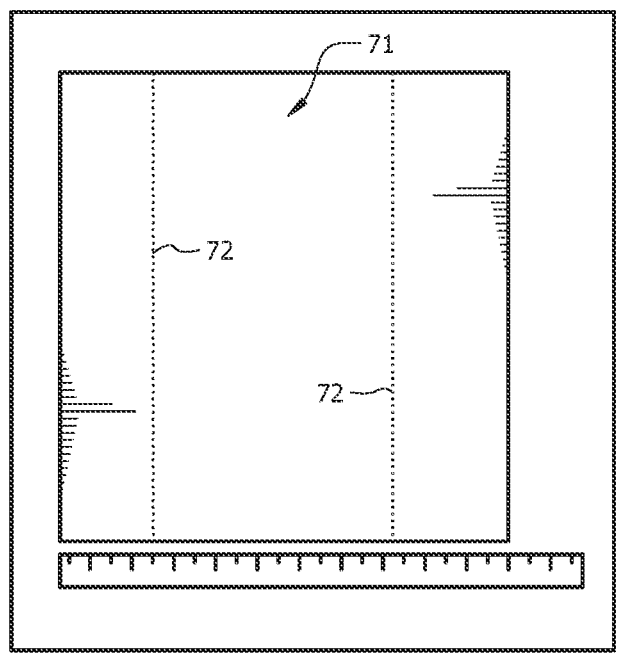
FIG. 2B is a depiction of a suitable select-a-size sheet paper towel test sample according to an embodiment of this disclosure.

In embodiments, the sample is cut in the machine direction (MD), with a paper cutter, and the perforations are avoided. 'Machine Direction' or 'MD' as used herein means the direction parallel to the flow of the paper towel through a paper-making machine. FIGS. 2A and 2B are depictions of suitable paper towel test samples 71 according to embodiments of this disclosure. In embodiments, the sample is cut from a full sheet roll of paper towel, and is cut a distance from perforations 72. In embodiments, sample 71 is cut from a full sheet roll of paper towel, and is cut ⅛ inch, ¼ inch or ½ inch off of the perforations 72, as shown in FIG. 2A. In embodiments, sample 71 is cut from a roll having smaller sheets, such as a 'select-a-size' roll, and is cut to a desired size while keeping the perforation(s) 72 as far from the center as possible, as shown in the embodiment of FIG. 2B. In embodiments, the desired size for the sample comprises a width (e.g., in a direction parallel to perforations 72) of about 11, or 7, or 4 inches, and a length (e.g., in a direction perpendicular to perforations 72) of about 10, 8, or 6 inches. To avoid excess generation of lint, the sample is obtained via cutting from the roll, rather than by tearing at the perforations 72. In order to further prevent foreign lint from contaminating the sample, when cutting the sample, the surface to be tested (i.e., the inside or the outside with reference to the roll) is maintained facing up.

The sample 71 is handled as minimally as possible and is not placed on any surface that may contaminate it prior to lint testing as described herein. Any surface with which the sample comes into contact (e.g., a lab bench surface, the surface of a paper cutter, etc.) is desirably a clean, lint-free surface. Such surfaces can be cleaned, for example, via commercially available cleaner (e.g., glass cleaner such as WINDEX® in a spray bottle) and/or lint-free wipes (e.g., ACCUWIPES SKU 29834). The cutting blade of a paper cutter utilized to cut the sample can be cleaned with compressed air prior to cutting each sample.

Figure 3:
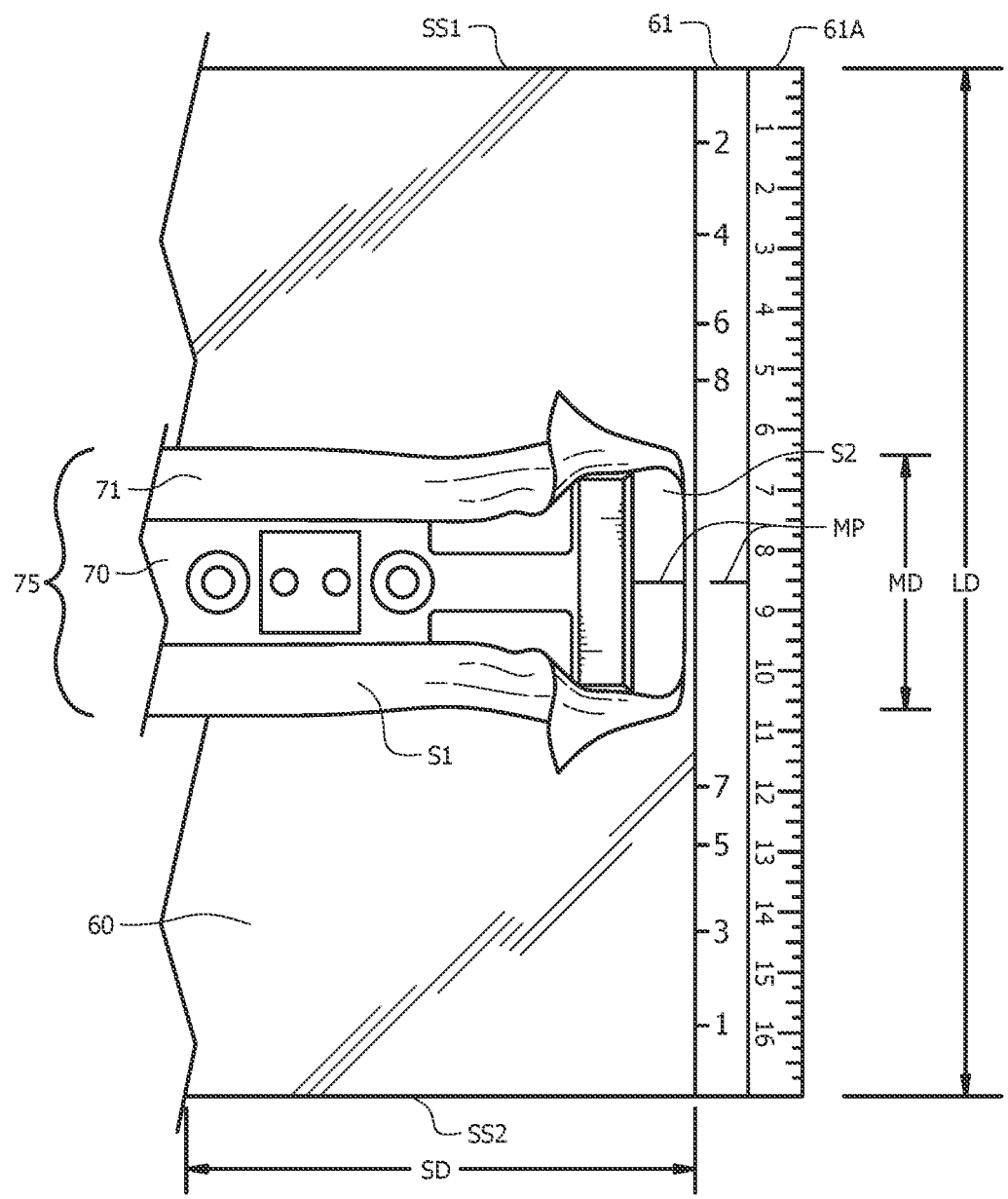
FIG. 3 is a schematic of a wrapped support positioned on a test or deposition surface, according to an embodiment of this disclosure.

Preparing the sample can further comprise wrapping a sample around a support. As the support imparts a pressure against the sample when wiped on the deposition surface, utilization of a two-sheet sample may, in embodiments, be employed to help prevent the outer sheet from tearing during the test. As depicted in FIG. 3, which is a schematic of a wrapped support 75 on a deposition surface 60, after being cut to the desired size, sample 71 can be wrapped around a support 70 to provide wrapped support 75.

The support can comprise any solid support around which sample 71 can be wrapped, and with which the plowing motion described hereinbelow for depositing lint can be performed. In embodiments, support 70 comprises a rubberized cushion material. In embodiments, the support is rectangular, having a long dimension or length and a short dimension or width. In embodiments, the support has a length in the range of from about 4 inches to about 11 inches, from about 7 inches to about 11 inches, or from about 10 inches to about 11 inches. In embodiments, the support has a width in the range of from about 2 inches to about 5 inches, from about 3 inches to about 5 inches, or from about 4 inches to about 5 inches. In embodiments, the support has a thickness or height in the range of from about 0.25 inch to about 3 inches, from about 0.25 inch to about 1.5 inches or from 0.25 inch to 0.75 inches. By way of non-limiting example, the support may comprise a modified SWIFFER® head, having a total weight of 1500 g and providing a 35 to about 40 square inch test area. The test area is the area of sample 71 the contacts deposition surface 60 during lint deposition. The test area may be in the range of from about 8 to about 55 square inches (in$^2$), from about 25 to about 45 in$^2$, from about 30 to about 40 in$^2$, or equal to about 10, 20, 25, 30, 35, 40, 45, 50, or 55 in$^2$.

Sample 71 can be placed onto deposition surface 60 onto which lint is to be deposited, described further below, with the machine direction MD of the towel sample 71 parallel with a long dimension LD of deposition surface 60, and the side of the paper towel sample to be analyzed 51 facing the deposition surface 60, and the other side S2 of sample 71 facing the support 70. In embodiments, sample 71 can be substantially centered on deposition surface 60, whereby the midpoint MP of the towel sample along the MD is aligned with the midway point MP of the long dimension LD of deposition surface 60. Sample 71 can be wrapped around support 70 by setting support 70 on sample 71 with the short dimension of support 70 parallel to the MD of sample 71, as shown in FIG. 3. The edges of sample 71 can be wrapped around support 70, and secured. For example, sample 71 can be secured around SWIFFER® head support 70 using the four inserts thereof.

A method of quantitating lint according to this disclosure further comprises depositing lint from the sample onto a test or deposition surface, as indicated at 30 of the flow diagram of FIG. 1. The lint is deposited by moving the sample on the surface in a specific pattern comprising a plurality of directional changes, as described hereinbelow. Deposition surface 60 may be rectangular, having a long dimension LD and a short dimension SD, as indicated in FIG. 3, and may be of a desired size. The desired size may comprise a short dimension in the range of from about 5 inches to about 12 inches, from about 7 inches to about 12 inches, or from about 11 inches to about 12 inches, and a long dimension in the range of from about 10 inches to about 24 inches, from about 14 inches to about 24 inches, or from about 17 inches to about 24 inches. The test or deposition surface may be a piece of glass, for example, a piece of black glass. In embodiments, the test or deposition surface comprises black glass (11¼ inch×17 inch×⅛ inch) with custom mounting pegs (and raised support stand and benchtop support stand, described below).

Figure 4:
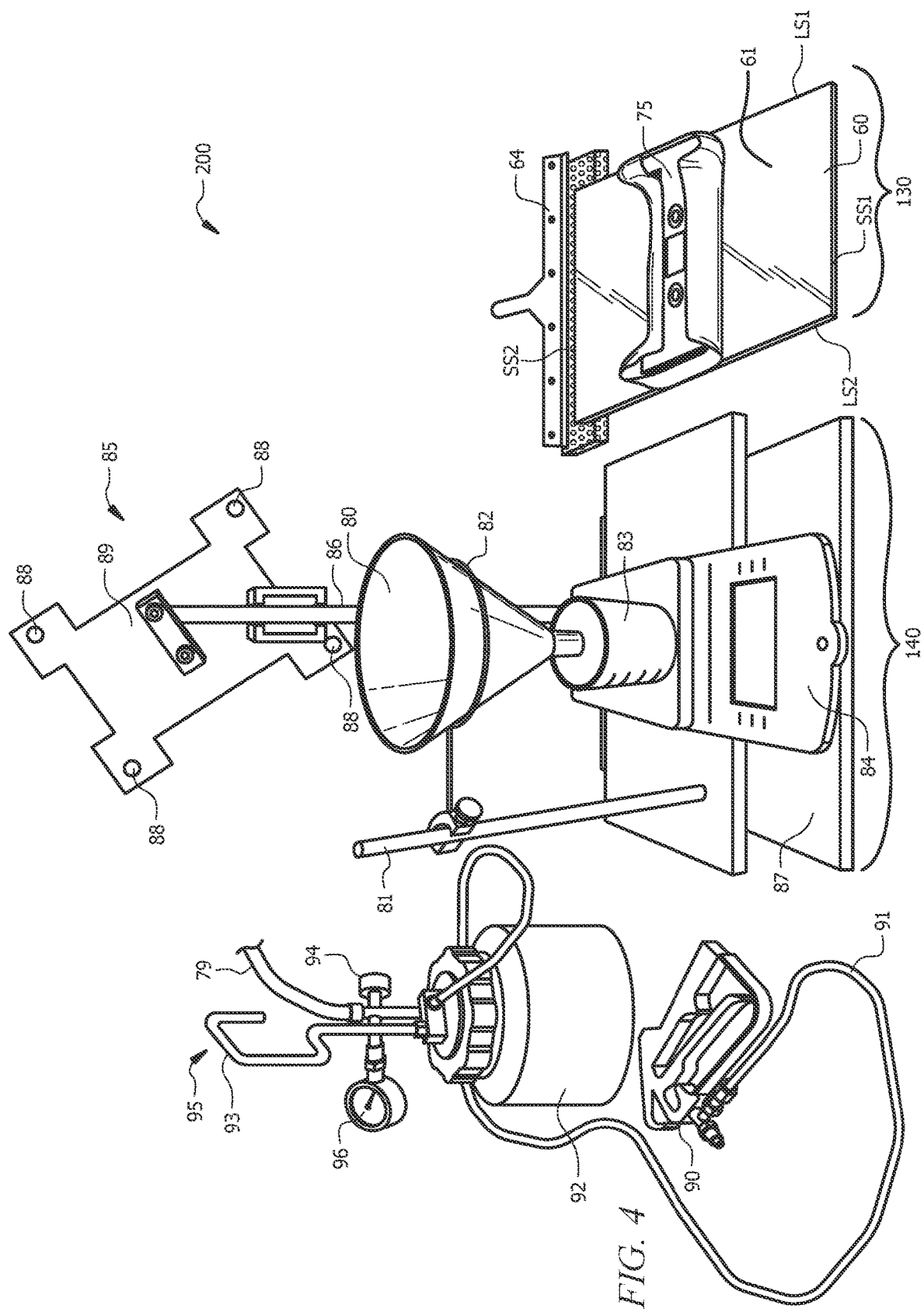
FIG. 4 is a schematic of a lint quantitation setup according to an embodiment of this disclosure.
Figures 5, 6:
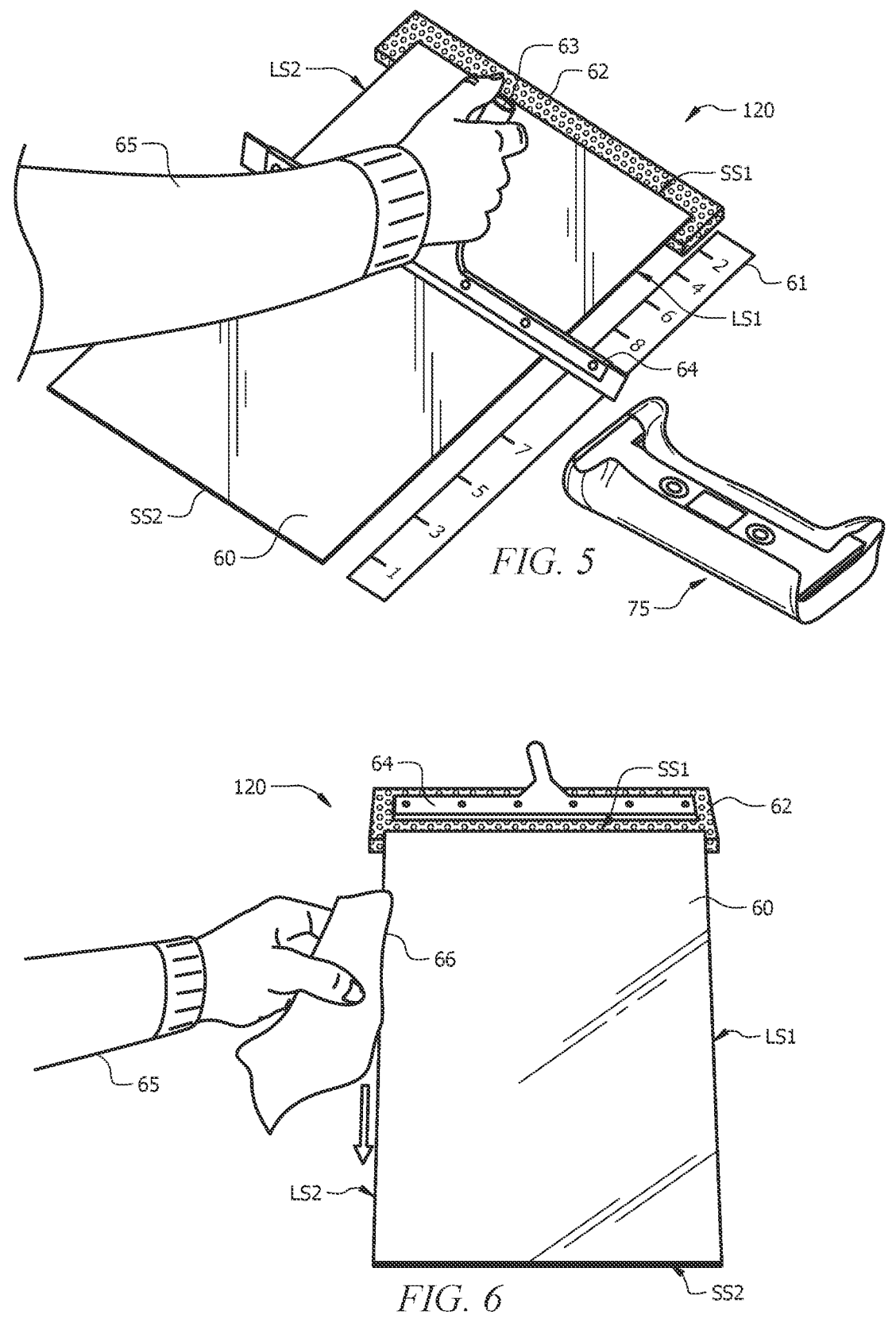

As seen in the embodiment of FIG. 4, which is a schematic of a lint quantitation setup 200 according to an embodiment of this disclosure, a setup for depositing lint 130 can comprise deposition surface 60. Deposition surface 60 can be rectangular, having a first long side LS1 along long dimension LD and a second long side LS2 along long dimension LD, a first short side SS1 along short dimension SD, and a second short side SS2 along short dimension SD. For manual lint deposition, deposition surface 60 may be positioned on a benchtop support stand with the long dimension LD leading away from an operator (65, as seen in FIG. 5).

In embodiments, a method of quantitating lint according to this disclosure further comprises cleaning the deposition surface 60, as indicated at step 20 of the flow diagram of FIG. 1, prior to depositing the lint thereupon. A method of cleaning deposition surface 60 will now be described with reference to FIG. 5, which is a schematic of a deposition surface cleaning setup 120 during squeegeeing, according to an embodiment of this disclosure. Cleaning the deposition surface 60 can comprise positioning deposition surface 60, for example, in a benchtop support stand. For manual operation of the method, deposition surface 60 can be positioned with the long dimension LD leading away from the operator 65. A lint-free sponge (not shown in FIG. 5) and squeegee 64 can be rinsed (e.g., with tap water), and the blades of squeegee 64 wiped with the lint free sponge. Any suitable lint-free sponge can be utilized, such as, for example, a #7271T32 sponge available from McMaster-Carr. Any suitable squeegee can be utilized, such as, for example, a #7334T35 window squeegee available from McMaster-Carr.

A separate lint-free sponge and a stream of tap water may be utilized at this point to clean the inside of a lint collection vessel (vessel 83 in FIG. 4) that will be utilized during lint collection, which is described further hereinbelow. For example, a lint-free sponge and a stream of tap water can be utilized to clean the inside of one or more lint collection vessels 83 comprising 500 mL glass or plastic beaker(s). A funnel (80 in the embodiment of FIG. 4) utilized during lint collection may also be prepared at this stage. For example, the lint collection vessel(s) 83 and the lint collection funnel 80 may be rinsed in a sink with tap water, to thoroughly clean any fibers from the surfaces thereof. The lint collection vessel(s) 83 and the lint collection funnel 80 may be rinsed a plurality of times, e.g., three times. In embodiment, the rinsed components are not dried, but rinse water is gently shaken off, and the vessel(s) are inverted, as on a countertop, to dry.

Cleaning the test or deposition surface at step 20 can comprise spraying substantially the entire surface with cleaner, which may comprise glass cleaner. The deposition surface may be sprayed with a plurality of sprays. In embodiments, the deposition surface 60 is sprayed with 6 sprays of cleaner, which provides about 6.0 grams (±0.2 g). A spray check as described vide infra can be performed to confirm that the desired amount of cleaner or wetting agent is applied via the sprayer.

To ensure the amount of wetting agent or surface cleaner, such as glass cleaner, utilized, a spray check can be performed whenever a spray head in a spray bottle utilized to spray the cleaner is changed, and/or whenever a spray bottle or pump is replaced, to verify the initial spray weight. A spray check can comprise placing a number of (e.g., two) sheets of paper towel on a balance; taring the balance; spraying the paper towel on the tared balance with three full pumps of the spray nozzle; noting the weight. In embodiments, the desired weight provided by three full sprays is about 3.0 grams (±0.2 g). Any suitable balance may be used. The balance may have a resolution of 1 gram.

After spraying the deposition surface with the desired amount of surface cleaner, squeegee 64 can be utilized to push the cleaner off the surface. Cellulose sponges 62 may be positioned along first short side SS1 of deposition surface 60, as indicated in FIG. 5, and squeegee 64 may be moved across deposition surface 60 such that cleaner squeegeed off deposition surface 60 is absorbed by cellulose sponges 62. Any suitable absorbent sponge may be utilized as sponge(s) 62.

As indicated in FIG. 6, which is a schematic of a deposition surface cleaning setup 120 during surface wiping, following squeegeeing of the cleaner off deposition surface 60 as shown in FIG. 5, a lint-free sponge 66, rinsed as described above, may be utilized to wipe the surfaces (i.e., the top, bottom, and sides SS1, SS2, LS1, and LS2) of deposition surface 60 free of lint.

Deposition surface 60 can be marked along the long dimension LD, as indicated in the embodiment of FIG. 3, to ensure repeatability of pattern passage during multiple tests. Alternatively, the markings may be associated with a support stand (e.g., a benchtop support stand) into which the surface is placed prior to deposition of lint thereupon. Such marking may be particularly useful for manual deposition of lint, although such markings may be useful for robotic operation as well, for ease of determination that the correct pattern is being followed. Although described herein with reference to the specific numbering scheme indicated in FIG. 3, other numbering schemes may be utilized, and are to be considered within the scope of this disclosure. The numbers on marker 61 are utilized during deposition of lint on the deposition surface in a specific pattern comprising a plurality of directional changes. Ruler 61A can be utilized to position the numbers on numbering scheme or marker 61. Numbering scheme or marker 61 of the embodiment of FIG. 3 comprises outermost numbers 1 and 2, which are 1.5 inches from the short sides SS1 and SS2 of deposition surface 60, respectively. Numbers 3 and 4 are positioned 1.5 inches inside (i.e., closer to midpoint MP than) markers 1 and 2, respectively; numbers 5 and 6 are positioned 1.5 inches inside markers 3 and 4, respectively; and numbers 7 and 8 are positioned 1 inch inside markers 5 and 6, respectively.

In embodiments, the herein disclosed lint quantitation method is a wet testing method. Accordingly, in embodiments, wrapped support 75 is lifted (manually or mechanically) off deposition surface 60, and deposition surface 60 is sprayed with a wetting liquid in wetting liquid sprayer 63 of FIG. 5, prior to lint deposition. For example, deposition surface 60 may be wetted with an amount of wetting liquid prior to placing wrapped support 75 back on deposition surface 60. The wetting liquid can comprise a glass cleaner. The amount of glass cleaner can comprise about 3, 4 or 5 grams of cleaner. Spraying the surface with wetting liquid can comprise wetting substantially the entire width of deposition surface 60 near midway point MP along the long dimension thereof, with the extent (e.g., equal to or greater than 80, 85, 90, 95, or 99 weight percent) of the concentrated spray falling within about the center two thirds of deposition surface (e.g., glass) 60 in the long dimension LD. The wetting liquid may be sprayed from a distance of from about 5 to about 7 inches above the surface, with the nozzle of wetting liquid sprayer 63 aimed at the center of deposition surface 60. With reference to FIG. 3, in embodiments, the sprays can wet the entire width along short dimension SD of deposition surface 60 near its vertical center or midpoint MP (i.e., between markings 7 and 8), and the bottom of any 'puddles' of concentrated spray may fall between the markings numbered 3 and 5, with minimal spray off the sides.

Following wetting of deposition surface 60, wrapped support 75 may be placed onto the sprayed surface, centering such that the midpoint MP (along the long dimension) of wrapped support 75 is aligned with the midpoint MP (along the long dimension) of deposition surface 60. Using the marking scheme of FIG. 3, the wrapped support 75 can be placed on sprayed deposition surface 60, such that the midpoint MP thereof is between markings 7 and 8.

Lint is deposited by moving wrapped support 75 over deposition surface 60 in a specific pattern, comprising a plurality of directional changes. In embodiments, wrapped support 75 is moved back and forth along the long dimension of deposition surface 60, keeping the long dimension of wrapped support 75 perpendicular to the LD of deposition surface 60. Without wishing to be limited by theory, changing direction via the plowing back and forth wiping motion of this disclosure may enhance lint deposition. For manual (i.e., human) operation, the wrapped support may be moved by placing index fingers at the top corners and thumbs at the bottom corners thereof.

When moving the wrapped support in the specific pattern to deposit lint, a plowing motion is utilized in which the wrapped support is tilted forward (e.g., in a direction of travel), whereby a leading edge of wrapped support 75 makes substantially full contact with deposition surface 60, and a trailing edge of wrapped support 75 is lifted a distance off deposition surface 60. The distance can be about 1/16, 1/8, or 1/3 inch. In embodiments, during plowing, the wrapped support is tilted forward at an angle of from about 0 to about 10 degrees, from about 0 to about 5 degrees, from about 1 to about 3 degrees, with the tilt angle of wrapped support being measured relative to the deposition surface 60. For example, for a 1/8 inch distance off deposition surface 60, the angle at which the wrapped support is tilted may be about 1.8 degrees from horizontal. Desirably, at least 50, 75 or 90 percent of the contact area of wrapped support 75 remains in contact with deposition surface 60 during plowing. Enough force is provided to the wrapped support to slide it across deposition surface 60, with no additional downward force. In embodiments, the force applied to the leading edge of wrapped support 75 is in the range of from about 0.1 to about 1 psi, from 0.1 to 0.5 psi, from 0.1 to 0.25 psi. Via the plowing motion, the wrapped support will rotate slightly forward toward the direction in which it is moving; when coming to a change in direction, the wrapped support is tilted in the opposite direction prior to moving in that opposite direction. This rotation allows the loose lint to be deposited on the surface. For manual operation, practicing of the plowing motion can be performed daily prior to testing.

Description of the movement utilized to deposit lint will now be provided. A plowing motion as described above is consistently utilized when moving the sample, and moving is intended to indicate 'moving in a plowing motion'. Initial back and forth pass(es) may be utilized to wet the sample 71/absorb the wetting liquid. For example, after placement at the MP of the sprayed surface, wrapped support 75 may be moved to the first short side SS1 of deposition surface 60 (such that the leading edge of wrapped support 75 is stopped between number 2 and the edge SS1), and a complete back and forth pass across the entire long dimension LD of deposition surface 60 performed, whereby the wrapped support 75 is moved to SS2 of deposition surface 60 (such that the leading edge of wrapped support 75 is stopped between number 1 and the edge SS2), and returned to SS1 (such that the leading edge of wrapped support 75 is stopped between number 2 and the edge SS1). Wrapped support 75 may then be moved back to the second short side SS2 of deposition surface 60 (such that the leading edge of wrapped support 75 aligns with number 1). Desirably, wrapped support 75 does not extend over first short side SS1 or second short side SS2 of deposition surface 60 while moving wrapped support 75 thereupon to deposit lint thereon. Desirably, in embodiments, there is substantially no movement of wrapped support 75 in a direction parallel to the short dimension SD of deposition surface 60.

Following the initial passes, wrapped support 75 is moved over deposition surface 60 in a specific pattern, comprising a plurality of directional changes. Such a specific pattern will now be described with reference to FIG. 3. As noted above, other specific patterns may be utilized in embodiments, so long as such patterns comprise a plurality of directional changes and movement is performed in a plowing motion.

Positioning of wrapped support 75 refers to alignment of the leading edge thereof with a 'position' along the LD of deposition surface 60. In embodiments, following the initial passes, wrapped support 75 is moved over deposition surface 60 in a specific pattern comprising a plurality of directional changes that occur at a plurality of positions. For example, the specific pattern may comprise 8 direction changes, at eight direction change positions, such as numbered positions 1 through 8 in the embodiment of FIG. 3. In embodiments, the specific pattern comprises at least 2, 3, 4, 5, 6, 7, or 8 direction change positions, and lint deposition comprises moving the wrapped support over the surface in a pattern comprising that number of direction changes.

In an embodiment, wrapped support 75 is brought to a first position (e.g., position 1 in the embodiment of FIG. 3), which is a direction change position of the specific pattern that is the most distal from MP on a first half of deposition surface 60 comprising first short side SS2. Direction of movement/plowing is changed, sliding wrapped support 75 to a second position (e.g., direction change position 2 in the embodiment of FIG. 3), which is located on the other half of deposition surface 60, which comprises first short side SS1. Positions 1 and 2 may be equidistant from the MP of deposition surface 60. Back and forth movement, via plowing, is continued to the other positions in the specified pattern, changing direction at each direction change position. Each subsequent position is on the opposite half of deposition surface 60 from the immediately prior direction change position, and each subsequent position on one half of deposition surface 60 (i.e., every other direction change position) is located a smaller distance from the MP of deposition surface 60 than the prior direction change position on that half of deposition surface 60 (i.e., a subsequent position on one side of deposition surface 60 is closer to the MP of deposition surface 60 than the position prior to the immediately prior position). For example, after moving to position 2 in the embodiment of FIG. 3, direction is changed, and plowing continues sequentially to positions 3, 4, 5, 6, 7, and 8. Positions 3 and 4, 5 and 6, and 7 and 8 are equidistant from the MP of deposition surface 60, with positions 3 and 4 closer to the MP of deposition surface 60 than positions 5 and 6, which are closer to the MP of deposition surface 60 than positions 7 and 8, as described hereinabove. After reaching the final position (e.g., position 8 in the embodiment of FIG. 3), wrapped support 75 is plowed to the center or MP of deposition surface 60, with its midpoint MP between positions 7 and 8.

In embodiments, depositing lint by moving the wrapped support over the surface in a specific pattern with or without the initial passes takes from about 40 to about 45 seconds, from about 15 to about 60 seconds, from about 25 to about 60 seconds, or from 35 to about 60 seconds to complete. In embodiments, all passes performed during lint deposition, including initial wetting passes, are completed within 40, 50, or 60 seconds. The duration may depend on the friction between the surface and the particular paper towel being tested. Some samples may grab and skip on the surface, and the speed can be reduced to prevent tearing of such samples.

Once the final position has been reached (e.g., the midpoint between direction change positions 7 and 8), wrapped support 75 can be lifted off deposition surface 60, and may be set aside. Note may be made of any tears or other unusual conditions of the spent sample. The spent sample may be removed from support 70 and disposed, after lint collection as described below.

In embodiments, tests are run in duplicate. In embodiments, tests of both sides of a paper towel are performed, in duplicate. Thus, in embodiments, four samples are subjected to lint deposition and collection as described herein, the samples comprising two samples wherein the inside of the paper towel (i.e. the side facing the roll when wound on a paper towel roll) is the test side 51 of the towel to be analyzed, and two samples wherein the outside (i.e. the side facing away from the roll when wound on a paper towel roll) of the paper towel is the test side 51 of the towel to be analyzed. The four samples may be cut prior to lint deposition of any of the samples. Alternatively, each sample may be cut immediately prior to lint deposition of that sample.

The lint quantitation method of this disclosure further comprises collecting the lint deposited on the surface, as indicated at step 40 of the flow diagram of FIG. 1. Description of lint collection will now be made with reference to FIG. 7, which is a schematic of a lint collection setup 140, according to an embodiment of this disclosure. In embodiments, lint collection is performed substantially immediately following lint deposition. The lint collection setup 140, as shown in FIG. 7, can be prepared/setup prior to, and/or may be situated alongside lint deposition setup 130, as shown in FIG. 4.

Figure 7:
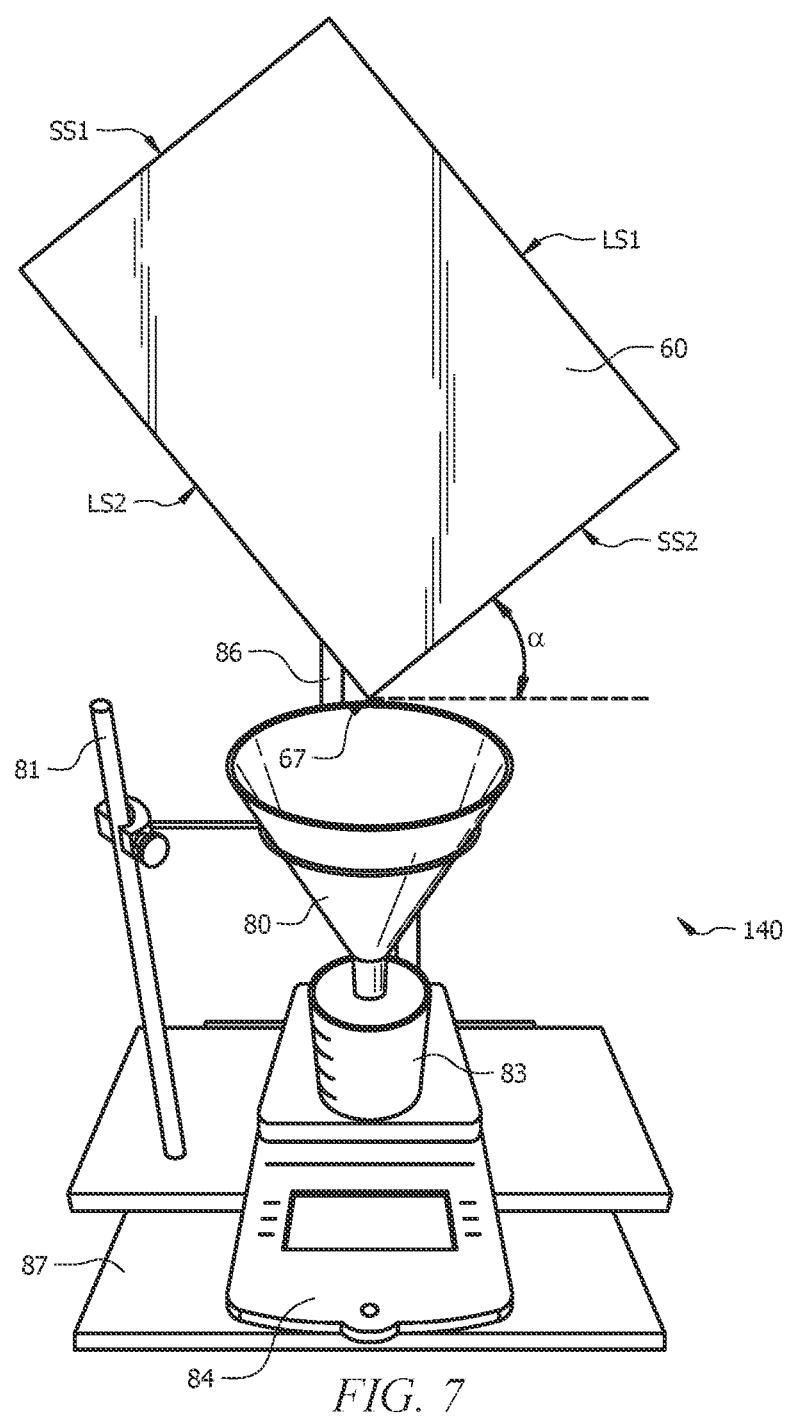
FIG. 7 is a schematic of a lint collection setup according to an embodiment of this disclosure.

Following lint deposition, the surface onto which lint has been deposited is placed in a raised support stand 85 comprising base 87, vertical member 86, and support attachment surface 89 (see also FIG. 4), and attached thereto, for example via positioning of one or more mounting pegs located on the bottom of deposition surface 60 into one or more holes 88 in support attachment surface 89 (four holes 88 shown in the embodiment of FIG. 7). In embodiments, deposition surface 60 is supported via raised support stand 85 such that a lowermost short side thereof (i.e., second short side SS2 in the embodiment of FIG. 7) is tilted an angle α from horizontal. In embodiments, a is in the range of from about 30 to about 60 degrees, from about 40 to about 50, or from about 43 to about 47 degrees. In embodiments, α is less than or equal to about 60, 50, 47, or 45 degrees.

Support stand 85 is positioned such that, when supported thereby at angle α, the lowermost point or corner 67 of deposition surface 60 is positioned over collection funnel 80, which may have been prepared (i.e., cleaned and allowed to dry), as described hereinabove. Collection funnel 80 may, in embodiments, have an inlet diameter of about 7, 8, or 9 inches. In embodiments, lowermost corner 67 of supported deposition surface 60 is substantially centered above collection funnel 80. Collection funnel 80 can be supported over balance 84 via a ring stand 81 comprising funnel support 82. Collection vessel 83, rinsed as described hereinabove, can be placed on balance 84, and the weight of the empty collection vessel tared.

Using a water sprayer 95, deposited lint is rinsed from deposition surface 60 through funnel 80 to collection vessel 83. Any suitable water sprayer may be utilized. In embodiments, a manual spray water bottle activated via squeezing the sides thereof is utilized. In embodiments, the water sprayer comprises a pressurized water canister and spray gun. In embodiments, water sprayer 95 comprises a pressurized water canister 92 and GUNJET® spray gun 90 number AA23L, a swivel 11990-10, enabling 360 degree operation, and a tip or nozzle TP0001 available from Spraying Systems Co.®, Wheaton, Ill. Although referred to herein as a 'water sprayer', in embodiments, water sprayer 95 is configured to provide water via substantially a single stream or jet of water, rather than a conventional spray or misting pattern. Water sprayer 95 may be configured to provide substantially a single stream of water having a stream diameter in the range of from about 0.01 inch to about 0.10 inch, from about 0.01 inch to about 0.05 inch, from about 0.03 inch to about 0.10 inch, or less than or equal to about 0.10 inch, 0.05 inch, or 0.03 inch. The water stream may be ejected from water sprayer 95 at a pressure in the range of from about 0.5 psi to about 10 psi, from about 0.5 psi to about 5 psi, from about 1.5 psi to about 3 psi. The water stream may be ejected from water sprayer 95 at a flow rate in the range of from about 0.5 mL/s to about 5 mL/s, from about 0.5 mL/s to about 4 mL/s, or from about 0.5 mL/s to about 3 mL/s.

A water sprayer 95 suitable for use according to embodiments of this disclosure will now be described with reference to FIG. 8, which is a schematic of a water sprayer 95 according to an embodiment of this disclosure. Water sprayer 95 comprises pressurized water canister 92, fluidly connected via line 91 to spray gun 90. Water sprayer 95 may further comprise pressure gauge 96, pressure relief valve/regulator 94 and canister handle 93. Prior to collecting lint, water sprayer 95 may be prepared for use as follows. The reservoir of water canister 92 is opened by unscrewing top 98. The reservoir is filled with lint-free water. The lint-free water may be deionized or distilled water, or a combination thereof. In embodiments, the water level to the fill line comprises about 2400 mL, which may be sufficient for testing approximately 8 to 9 towel samples 71. Top 98 is screwed back on water canister 92. The water sprayer 95 is pressurized by opening a shutoff valve on house compressed air (and air inlet line 79), setting the mainline regulator to 10 psi, and setting spray can regulator 94 to 2.5 psi. The flowrate on water sprayer 95 can be checked by utilizing a timer and graduated cylinder (e.g., a 50 mL graduated cylinder), as known in the art. In embodiments, the desired flowrate is in the range of from about 20 to about 22 mL per 10 seconds. The flowrate may be checked each time water is added to the reservoir, as reduced pressure, air in line 91, or a clog in a spray nozzle 97 of spray gun 90 may reduce the flowrate.

Initial filling and subsequent refilling of the reservoir can introduce bubbles into line 91. Prior to use, ensure that there are no bubbles in line 91 connecting water canister 92 to spray gun 90, eliminating bubbles by activating the sprayer (i.e., depressing trigger handle 99) to bleed bubbles out of line 91.

As noted above, using water sprayer 95, deposited lint is rinsed from deposition surface 60 into through funnel 80 to collection vessel 83. Water may be sprayed with tip or nozzle 97 a desired distance away from deposition surface 60, for example, from about 1 to about 3, or about 1, 2, or 3 inches from deposition surface 60. Spraying may be directed inward (i.e., away from the edges or sides of deposition surface 60) at an angle from perpendicular with deposition surface 60, to minimize/avoid splashing and overspray. Beginning at bottom edges of deposition surface 60, a perimeter can be rinsed along both bottom-pointing sides/edges (SS2 and LS2 in the embodiment of FIG. 7), whereby rinse water flows towards lowermost corner 67, through collection funnel 80, into collection vessel or beaker 83. Spraying is performed in a manner that minimizes or prevents beading of rinse water along edges of deposition surface 60, as such beads (potentially carrying lint) may drip off deposition surface 60 outside of funnel 80, and thus vessel 83. The perimeter may comprise the outermost approximately 1, 2, or 3 inches of deposition surface 60, in embodiments. Once the perimeters of bottommost sides SS2 and LS2 are wet, spraying can be continued on the innermost portion of deposition surface 60 from top to bottom until the entire deposition surface 60 is wet. Upper edges (e.g., sides SS1 and LS1, in the embodiment of FIG. 7) are then rinsed inward to minimize/avoid dripping/splashing outside of funnel 80, and thus vessel 83. Rinsing may continue in a back and forth wave motion across the entire width of deposition surface 60 slowly working across and down until a desired volume of surface rinse water has been collected in collection vessel 83. The desired volume of surface rinse water may be in the range of from about 50 grams to about 5000 grams, from about 100 grams to about 1000 grams, from about 200 grams to about 500 grams, or from about 150 grams to about 200 grams. In embodiments, the desired volume of surface rinse water is about 150, 160, 170, 180, 190, 200, 250, or 300 grams.

Collection funnel 80 can then be rinsed, primarily on the region where rinse water has dripped from deposition surface 60. Funnel rinsing may be performed until a desired total rinse water is present in collection vessel 83. The desired total rinse water may comprise 10, 20, or 30 grams more water than the desired volume of surface rinse water, such as noted hereinabove. In embodiments, the desired total rinse water may comprise from about 160 to about 230, from about 150 to about 300, or from about 50 to about 5000 grams of water. In embodiments, the desired total amount of rinse water comprises about 180, 200, 220, 230, 240, or 250 grams (±0.5 grams) of rinse water. In embodiments, the total rinse water volume is within 1.0 grams of the desired total rinse water volume.

Following rinsing of deposition surface 60 and funnel 80, collection vessel 83 may be covered, for example with plastic cling wrap, and secured, for example, with a rubber band. The vessel may be labeled with sequential numbers, for example, using painter's tape and a marker. The used towel sample 71 may be removed from support 70, and discarded. Surface cleaning, lint deposition, and lint collection may be repeated for the desired samples, e.g., duplicates of inside and outside surfaces of paper towel. In embodiments, for each product tested, four repetitions are tested in the order: outside, inside, outside, inside.

Testing may include one or more quality control (QC) sample (outside and inside of a known paper towel product), and one or more blank per tester. A blank consists of a complete sample testing as described hereinabove, without the lint deposition step. A blank may be run prior to and/or subsequent testing of a product (e.g., testing of the outside; inside; outside; inside thereof). The blank reading utilized can be an average of multiple blank runs, for example, an average of the FQA values (described further below) obtained for a blank run preformed prior to testing the sample, and a blank run performed subsequent thereto. In embodiments, the cleaning of deposition surface 60, such as described herein, provides for a blank having a total fiber area of lint, calculated as described below) in the range of from about 0.1 mm$^2$ to about 1.0 mm$^2$, from about 0.1 mm$^2$ to about 0.8 mm$^2$, or from about 0.2 mm$^2$ to about 0.3 mm$^2$. In embodiments, the total fiber area of lint determined for the blank is less than or equal to about 1.2 mm$^2$, 1.0 mm$^2$, 0.8 mm$^2$, 0.7 mm$^2$, 0.6 mm$^2$, 0.5 mm$^2$, 0.4 mm$^2$, 0.3 mm$^2$, or 0.2 mm$^2$.

Samples can be retested if there is excessive tearing of the sample, if the total collected rinse water exceeds 1 gram more than the desired total rinse water volume (e.g., if the total collected rinse water is 201 grams, and the desired total rinse water is 200 grams), if the rinse water is depleted in pressurized water canister 92, or any other deviance from the procedure is encountered.

A lint quantitation method according to this disclosure further comprises determining the amount of collected lint, as indicated at step 50 of the flow diagram of FIG. 1. Determining the amount of collected lint can comprise measuring and/or calculating the amount of collected lint. A Fiber Quality Analyzer (FQA) may be utilized to measure the amount of collected lint. At least a portion of the total rinse water in collection vessel 83 containing collected lint is subjected to fiber quality analysis to determine the amount of collected lint. In embodiments, fiber quality analysis is performed within 24 hours of lint collection. In embodiments, an OPTEST® fiber quality analyzer model FQA-360, available from OpTest Equipment Inc. (900 Tupper St.-Hawkesbury, ON, K6A3S3 Canada) is utilized to determine the number of lint fibers in collection vessel 83. The OPTEST® Fiber Quality Analyzer has become a standard in the paper industry for determining fiber length distributions and fiber counts (above a certain minimal length, which keeps decreasing periodically, as upgrades are made).

Before conducting FQA, the total volume of collected rinse water (e.g., 200 mL) is mixed, for example, by pouring back and forth a number of (e.g., 3) times to ensure adequate mixing of the sample. An aliquot (e.g., 50 mL) can then be subsampled from this beaker, transferred to an FQA test beaker, and diluted to a desired test sample volume (e.g., 600 mL (grams)) to provide an FQA test sample prior to FQA testing. Alternatively, the entirety of the collected rinse water is utilized and diluted to provide an FQA test sample, as long as the FQA is operable to count fibers up to the number of fibers therein (i.e., so long as the total number of fibers in the FQA test sample does not exceed the FQA counting capacity).

To reduce the overall run time involved in the lint analysis (in embodiments, up to 50%), the number of cycles utilized during FQA analysis testing can be reduced. For example, if utilizing 7-8 cycles results in less than 1% of the overall fiber remaining in the test beaker, while one cycle results in approximately 82% of the total fiber being counted, to save time and increase efficiency, the lint number can be reported as the first cycle lint count divided by 0.82. While not an exact number, this method can be used, in embodiments, to approximate the total lint from the aliquot while reducing the run time.

The fiber quality analyzer provides an average fiber length, average fiber width, and fiber count. As a large number or fiber count of very small fibers (e.g., microfibers) may not be perceptible visibly (for example, to a consumer), the amount of lint can be reported as a total fiber area (TFA), as differences in TFA may be meaningful visually and thus better correlate with (consumer) perception of how much lint is left behind after utilizing a product in a wiping application. Determining the amount of lint may thus further comprise calculating the amount of lint. For example, the total fiber area of the sample can be determined according to Equation (1):

$$\text{Total Fiber Area (mm}^2\text{)} = [((\text{Avg. Fiber Length (mm)}) \times (\text{Avg. Fiber Width (mm)}) \times \text{Fiber Count}) - (\text{TFA of Blank})] \quad (1)$$

The total fiber area of the blank is determined as the average fiber length times the average fiber width times the fiber count for the blank sample, processed as described hereinabove.

For each sample, the fiber area may be reported as an average of the values obtained for the samples from that paper towel roll, and may include the standard deviation thereof, determined as known to those of skill in the art. For example, the average of the TFAs obtained from inside and outside, and/or replicate samples thereof may be provided. The minimum and maximum fiber areas may also be reported, as well as the number of replicates for each sample. TFAs may be reported in any desired units, for example mm$^2$, and may be reported to the nearest tenth (e.g., the nearest 0.1 mm$^2$). Reporting may further comprise stating any deviations from the standard procedure described herein, and any unusual features or characteristics of the sample.

EXAMPLES

The disclosure having been generally described, the following examples are given as particular embodiments of the disclosure and to demonstrate the practice and advantages thereof. It is understood that the examples are given by way of illustration and are not intended to limit the specification or the claims to follow in any manner.

Example 1: Manual Method of Determining Amount of Lint Shed from a Paper Towel During Wiping A method according to this disclosure is utilized to determine the amount of lint shed from a paper towel during a wiping motion.

Paper towel samples 71 are preconditioned and conditioned according to Standard Test Method TAPPI TM-402. Specifically, a roll of paper towel is placed in an environment under a standard conditioning and testing atmosphere of 72° and 50% relative humidity, for a time of 2 hours.

Test samples are cut in the machine direction (MD) with a paper cutter, avoiding the perforation. As seen in FIG. 2A, for full sheet rolls, cut sample ⅛-in. to the left of the perforations. As seen in FIG. 2B, for rolls with smaller (e.g., 'select-a-size') sheets, cut a 10-in. length keeping the perforations as far away from center as possible. Do not cut samples ahead of time. Cut each sample just prior to testing.

Cut sample using a paper cutter to avoid generation of excess lint. Do not tear sample at perforations. When cutting samples, keep testing surface (inside or outside) of towel facing up to avoid foreign lint from contaminating sample. Do not unnecessarily handle samples or lay samples on any surface that may contaminate them. Clean lab bench surface and paper cutter surface using glass cleaner in spray bottle and lint-free wipes (ACCUWIPES, SKU #29834). Clean cutting blade with compressed air prior to cutting each sample.

Figure 8:
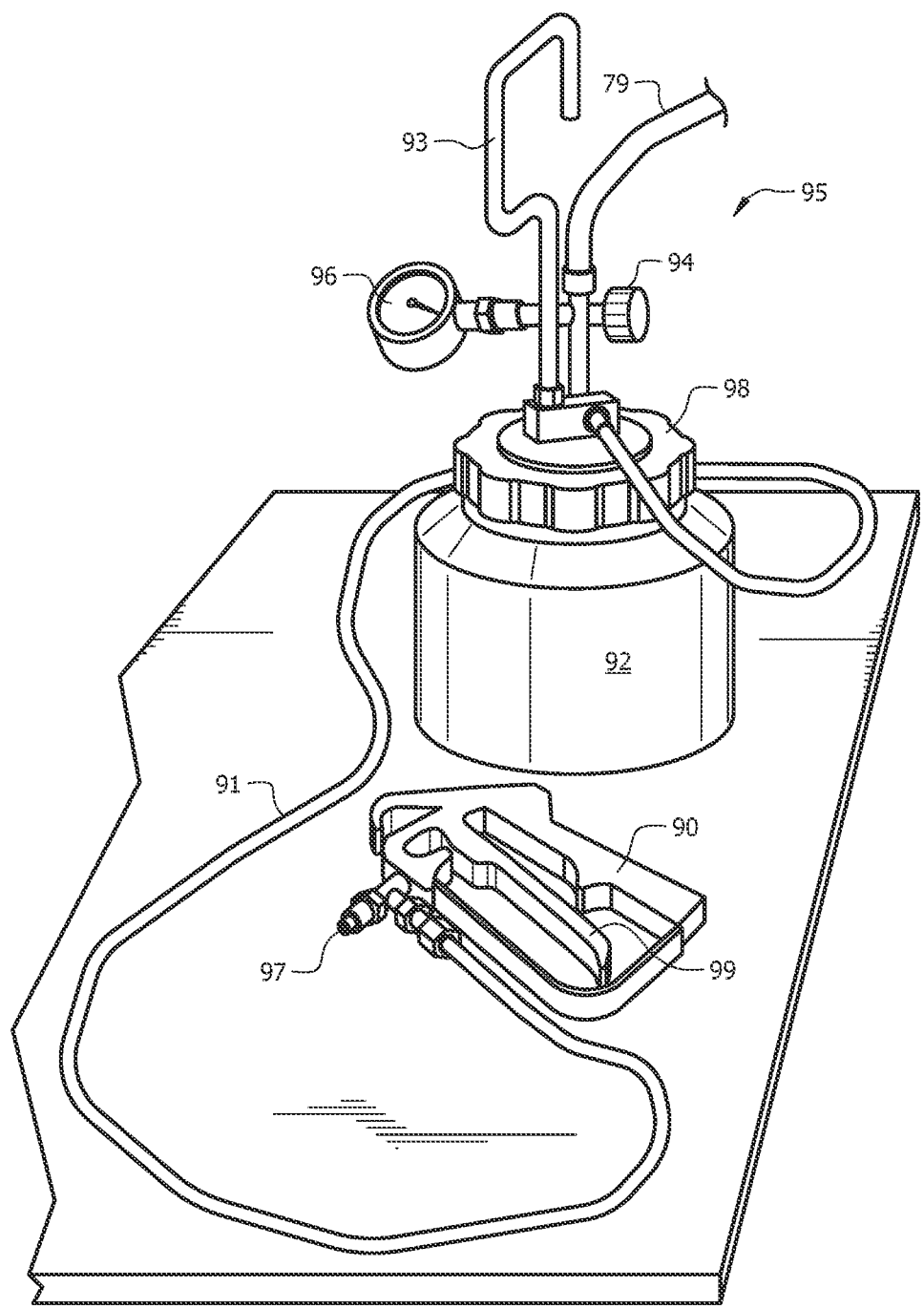
FIG. 8 is a schematic of a water sprayer according to an embodiment of this disclosure.

Set-up a water sprayer 95 comprising a pressurized water canister 92 and GUNJET® spray gun AA23L 90, swivel 11990-10, and tip TP0001 97 available from Spraying Systems Co® as shown in FIG. 8. Open the reservoir on water canister 92 by unscrewing top 98. Fill reservoir with deionized water. Water level to the fill line at shoulder is approximately 2400 mL, sufficient for testing approximately 8-9 samples 71. Check to see that the reservoir is full before use.

Screw top 98 back on canister 92. Pressurize water sprayer 95 by opening the shutoff valve on the house compressed air, setting the mainline regulator to 10 psi and setting the spray can regulator 94 to 2.5 psi. Check the flowrate on water sprayer 95 by using a timer and (e.g., 50 mL) graduated cylinder, to ensure a flowrate of 20-22 mL per 10 sec. Check the water sprayer flowrate after adding water to reservoir, as reduced pressure, air in line 91, or a clog in spray nozzle 97 may reduce the flowrate.

Ensure that there are no air bubbles in line 91 connecting the pressurized water canister 92 to spray gun 90. Initial filling and subsequent refilling of the reservoir can introduce air bubbles in line 91. Eliminate any bubbles by activating sprayer via trigger handle 99 to bleed bubbles out of line 91.

Subsequent to testing, water sprayer 95 may be depressurized by turning off the airline ball valve, adjusting the mainline regulator 94 to 0 psi, and releasing canister pressure by pulling out relief valve by ring. Ensure that there is no pressure in water canister 92 before opening top 98.

Place 2 full sheets of extra paper towel on a balance having 1 gram resolution. Tare the balance. Check the amount of glass cleaner delivered by three full pumps of the spray nozzle. Spray 3 full sprays of glass cleaner onto paper towels and note weight. Three full sprays should equal 3.0 grams (±0.2 g). Check initial spray weight and when pump head on spray bottle is changed or a when a bottle/pump is replaced.

Before beginning testing for the day, practice spraying glass or deposition surface 60 with glass cleaner, and practice the 'plowing' motion with a modified SWIFFER® head support 70 having 1500 grams total weight and a 30 sq. inch test surface.

Place deposition surface 60 (e.g., black glass) in benchtop support stand with long dimension LD away from operator 65. A black glass deposition surface 60 may be an 11¼in.× 17-in.×⅛-in. glass with custom mounting pegs and raised support stand 85, and benchtop support stand may be available from Research Dimensions, 1720 Oakridge Road, Neenah, Wis. 54956. Verify that black glass deposition surface 60 is marked along the long dimension so that the outside marks (Numbers 1 and 2 in FIG. 3) are 1.5-in. in from the short sides SS2 and SS1, respectively, and the other marks are spaced 1.5-in. and 1-in. apart as shown in FIG. 3.

Rinse a lint free sponge 66 (McMaster-Carr part #7271T32) and squeegee 64 (14-in width, McMaster-Carr window squeegee part #7334T35) with tap water, then wipe the squeegee blades of squeegee 64 with the lint free sponge 66. Use a separate lint free sponge 66 and a stream of tap water to clean the inside of 500 mL beaker collection vessels 83. Rinse a funnel 80 (8-in. diameter) and 500 mL beakers with shower sprayer in the sink with tap water to thoroughly clean any fibers from the surfaces thereof, rinsing at least three times. Do not dry, but gently shake the water off and invert beakers on countertop.

Spray the entire surface of the black glass deposition surface 60 with glass cleaner (6 sprays) via liquid sprayer 63. Use the squeegee 64 to push the glass cleaner off the back (far short side SS1) of the black glass deposition surface 60, as illustrated in FIG. 5. Cellulose sponges 62 can be used to absorb the glass cleaner squeegeed off the black glass deposition surface 60, as also illustrated in FIG. 5. Use the rinsed lint free sponge 66 described at the beginning of this 'Lint Deposition' section to wipe the top, bottom and side edges of black glass deposition surface 60 free of lint (FIG. 5).

As noted in 'Sample Preparation', cut each two-sheet sample 71 immediately before testing, in order to avoid contamination of the sample with foreign lint. Place a two-sheet sample 71 onto the center of the black glass deposition surface 60 with the machine direction (MD) of the towel parallel with the long dimension LD of the black glass deposition surface 60, and the surface to be tested 51 against the black glass deposition surface 60. Test both outside and inside surfaces for each sample 71, unless otherwise requested. Tests may be run in duplicate: outside and inside of towel for a total of four tests per sample.

Set the SWIFFER® head support 70 on the center of towel sample 71 with its short dimension parallel to the MD of towel sample 71. Wrap the edges of towel sample 71 around the SWIFFER® head support 70, securing it using the four inserts, as illustrated in FIG. 3. Lift the wrapped support 75 comprising SWIFFER® head support 70 and towel sample 71 off the black glass deposition surface 60 with one hand. With the other hand holding the glass cleaner spray bottle (liquid sprayer 63) 5-7 in. above the black glass deposition surface 60 and aiming the nozzle thereof at the center of the black glass deposition surface 60, spray the black glass deposition surface 60 with 3 full sprays (approx. 3 grams) of glass cleaner. The sprays should wet the entire width of the black glass deposition surface 60 near its vertical center, with the bottom of any 'puddles' of concentrated spray falling between the markings numbered '3' and '5' on the black glass deposition surface 60, with minimal spray off the top edge or side SS1 onto the lab bench behind. The sprays should fall mostly within the (vertical) center two-thirds (⅔) of black glass deposition surface 60.

Set the wrapped support 75 comprising SWIFFER® head support 70 and towel sample 71 back onto the sprayed black glass deposition surface 60 centering the SWIFFER® head support between the numbers '7' and '8' markings. Grasp the wrapped SWIFFER® head support 70 by placing index fingers at the top corners and thumbs at the bottom corners thereof. When moving wrapped support 75, maintain rotation of the SWIFFER® head support 70 slightly towards the direction it is moving, referred to herein as 'plowing'. When coming to a change in direction, roll the SWIFFER® head 70 to the opposite direction before changing direction. This rotation allows the loose lint to be deposited on black glass deposition surface 60.

Rub the wrapped support 75 comprising SWIFFER® head support 70 and towel sample 71 back and forth in the long dimension LD of the black glass deposition surface 60, keeping the long dimension of the wrapped support 75 perpendicular to the long dimension LD of black glass deposition surface 60. Begin by sliding the wrapped support 75 to the top (i.e., SS1) of the black glass deposition surface 60, complete a back and forth pass across the entire surface of the black glass deposition surface 60, returning to the top (i.e., SS1). Do not apply any additional downward force to the weighted wrapped support 75. The force applied is just that to slide the wrapped support 75 across the black glass deposition surface 60. Perform sliding with a 'plowing' motion, in which the SWIFFER® head support 70 is tilted slightly forward, with the 'leading' edge making full contact with the black glass deposition surface 60, and the 'trailing' edge lifted⅛-inch. After the initial passes, glide the SWIFFER® head support 70 until the leading edge reaches the number 1 position. Change directions and switch the direction of the 'plow', sliding to number 2 at the top (i.e., SS1) of the black glass deposition surface 60. Continue a back and forth process, moving sequentially number to number until reaching number 8. Then plow to the center MP of the glass (between '7' and '8'). The lint deposition process (as described in this paragraph) may take 40-45 seconds to complete; this will depend upon the friction between the black glass deposition surface 60 and the particular paper towel being tested. Some towel samples 71 may grab and skip on black glass deposition surface 60, and speed may then be reduced to prevent ripping of the sample 71. All passes can be completed within 50 seconds.

After the final center position (i.e., the MP, between the numbers '7' and '8' markings) has been reached, lift the wrapped support 75 off black glass deposition surface 60 and set aside. Note any tears or unusual conditions. (Remove and dispose of the used towel sample 71 later.)

The lint collection setup 140, as shown in FIG. 7, can be prepared prior to, and may be situated alongside lint deposition setup 130, as shown in FIG. 4. A compressed air cleaner can be utilized to clean lint from the countertop prior to setup. Immediately after depositing lint as described in 'Lint Deposition Procedure' section above, lift the black glass deposition surface 60 with deposited lint and place it in the raised support stand 85 above the funnel 80, ensuring that the mounting pegs of the black glass deposition surface 60 are firmly positioned in the respective holes 88 in support attachment surface 89. Tip the long dimension LD of the black glass deposition surface 60 to about 45 degrees from horizontal with the lowermost corner 67 of the black glass deposition surface 60 pointing into funnel 80.

Ring stand 81 next to balance 84 supports funnel 80 over balance 84. Place a rinsed beaker collection vessel 83 on balance 84 as shown in FIG. 7. Tare the weight of the empty beaker collection vessel 83. Use the spray gun 90 with the nozzle 97 about 2 inches from the surface of black glass deposition surface 60 to rinse the lint into funnel 80. Spray inward at an angle to avoid splashing and overspray. Starting at the bottom edges/sides SS2/LS2 of the black glass deposition surface 60, rinse a 2-inch perimeter along both bottom-pointing edges/sides SS2/LS2 so that the rinse water flows towards the lowermost corner 67 and into beaker 80. Avoid beading of water along edges that may drip off taking lint particles therewith. Once the 2-inch perimeters of the bottom edges are wet, continue wetting the innermost portion of black glass deposition surface 60 from top to bottom until the entire glass surface is wet. Rinse the upper edges inward to avoid dripping/splashing outside beaker collection vessel 83. Continue rinsing in a back and forth wave motion across the entire width of black glass deposition surface 60, slowly working across and down until there are approximately 180 grams of rinse water in beaker collection vessel 83.

Carefully top off beaker collection vessel 83, while rinsing funnel 80, (especially on the region where water has dripped from black glass deposition surface 60) until there are 200 grams (±0.5 g) of rinse water in beaker collection vessel 83. Do not exceed 201 grams. Cover beaker collection vessel 83, for example, with cling wrap, and secure, for example with a rubber band. Label beaker collection vessels 83, for example, with sequential numbers using painter's tape and a marker.

Remove used towel sample 71 from the SWIFFER® head support 70 and discard. Repeat cleaning, depositing lint, and collecting lint for all samples. Record, including sample number and sample description, may be kept in a laboratory notebook. For each product (e.g., paper towel roll) tested, four reps can be tested in the following order: outside; inside; outside; inside. Each day of testing can include one QC sample (outside: inside) and one blank per operator 65. A blank consists of a complete sample testing procedure without the glass cleaner and without the towel sample 71 and SWIFFER® head steps, i.e., without the lint deposition procedure described above.

When testing is completed, ensure that the main airline of water sprayer 95 is in the off position and that the regulator 94 thereof has been closed (zero gauge pressure). Relieve pressure from water sprayer 95 and airlines by pulling open the relief valve on the spray canister 92.

Have the contents of beaker collection vessels 83 analyzed (for example, in a Fiber Lab) for FQA Fiber Counting utilizing an OPTEST® Fiber Quality Analyzer, Model FQA-360 available from: OpTest Equipment Inc., 900 Tupper Street, Hawkesbury, OT, Canada K6A 353.

Samples may be retested if there is excessive tearing of sample 71 during lint deposition, if collected rinse water during lint collection exceeds 201 grams, if DI water is depleted in pressurized spray canister 92 during lint collection, or any other change from the test method is encountered. FQA can be done no later than one day after testing/lint collection.

From the FQA results, including average fiber length, L (mm), average fiber width, W (μm), and fiber count FC (number), determine the amount of paper towel lint as the Total Fiber Area, TFA ($mm^2$), using Equation (1) hereinabove: TFA=([L×(W/1000)×FC]−Blank), wherein Blank ($mm^2$) is calculated using the FQA data (i.e., L×W×FC) the same way as for a sample. For each sample, report the average, standard deviation, minimum and maximum test results to the nearest 0.1 $mm^2$ and the number of replicates for each. Clearly state any deviations from the standard procedure, and note any unusual features or characteristics of each sample 71.

ADDITIONAL EMBODIMENTS

The particular embodiments disclosed above are illustrative only, as the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and all such variations are considered within the scope and spirit of the present disclosure. Alternative embodiments that result from combining, integrating, and/or omitting features of the embodiment(s) are also within the scope of the disclosure. While compositions and methods are described in broader terms of "having", "comprising," "containing," or "including" various components or steps, the compositions and methods can also "consist essentially of" or "consist of" the various components and steps. Use of the term "optionally" with respect to any element of a claim means that the element is required, or alternatively, the element is not required, both alternatives being within the scope of the claim.

Numbers and ranges disclosed above may vary by some amount. Whenever a numerical range with a lower limit and an upper limit is disclosed, any number and any included range falling within the range are specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an", as used in the claims, are defined herein to mean one or more than one of the element that it introduces. If there is any conflict in the usages of a word or term in this specification and one or more patent or other documents, the definitions that are consistent with this specification should be adopted.

The following are nonlimiting, specific embodiments in accordance with the present disclosure:

A: A method for quantitating the amount of lint shed from a paper towel, the method comprising: preparing a sample of paper towel to be analyzed; depositing lint from the sample onto a surface, which has been cleaned, by moving the sample thereupon in a specific pattern comprising a plurality of directional changes; collecting the lint deposited on the surface; and determining the amount of collected lint.

B: A method for determining the amount of lint shed from a paper towel, the method comprising: preparing a sample of paper towel to be analyzed; depositing lint from the sample onto a substantially lint-free surface by moving the sample thereupon in a specific pattern; collecting the lint deposited on the surface; measuring the number, the average length, and the average width of the fibers in the collected lint; and calculating the amount of collected lint as the total fiber area ($mm^2$), by multiplying the average fiber length (mm) by the average fiber width (mm) and the fiber count and subtracting a blank therefrom, wherein the blank is calculated as the amount of lint collected from the substantially lint-free surface in the absence of the depositing step.

C: A method for quantitating the amount of lint shed from a paper towel, the method comprising: cleaning a rectangular deposition surface having a short dimension and a long dimension, wherein cleaning comprises spraying the entire surface with glass cleaner, using a substantially lint-free squeegee to push the glass cleaner off one of two short sides of the surface, and using a substantially lint-free sponge to wipe the edges of the surface substantially free of lint; preparing a sample of paper towel to be analyzed; depositing lint from the sample onto the cleaned surface by moving the sample thereupon in a specific pattern; collecting the lint deposited on the surface; and determining the amount of collected lint.

D: A method for quantitating the amount of lint shed from a paper towel, the method comprising: preparing a sample of paper towel to be analyzed; depositing lint from the sample onto a substantially lint-free surface by moving the sample thereupon in a specific pattern; collecting the lint deposited on the surface, wherein collecting the lint deposited on the surface comprises, substantially immediately upon depositing lint from the sample onto the surface, washing the deposited lint from the surface into a tared, cleaned, empty vessel; and determining the amount of collected lint.

E: A method for quantitating the amount of lint shed from a paper towel, the method comprising: preparing a sample of paper towel to be analyzed, wherein preparing the sample comprises wrapping the sample around a solid support, to provide a wrapped support; depositing lint from the sample onto a surface, which has been cleaned, by moving the sample thereupon in a specific pattern comprising a plurality of directional changes; collecting the lint deposited on the surface; and determining the amount of collected lint, wherein the surface is substantially rectangular, having a long dimension and a short dimension, wherein the solid support is substantially rectangular, having a long dimension and a short dimension, and wherein wrapping the sample around the solid support further comprises placing the solid support on the sample on a side of the sample opposite a side of the sample to contact the surface during lint deposition and wrapping the sample around the solid support, with a machine direction of the sample parallel to the short dimension of the solid support.

F: A method for quantitating the amount of lint shed from a paper towel, the method comprising: preparing a sample of paper towel to be analyzed, wherein preparing the sample comprises wrapping the sample around a solid support, to provide a wrapped support, wherein wrapping the sample around the solid support further comprises placing the solid support on the sample on a side of the sample opposite a side of the sample to contact the surface during lint deposition and wrapping the sample around the solid support; depositing lint from the sample onto a surface, which has been cleaned, by moving the sample thereupon in a specific pattern comprising a plurality of directional changes; collecting the lint deposited on the surface; and determining the amount of collected lint.

Each of embodiments A, B, C, D, E, and F may have one or more of the following additional elements: Element 1: wherein the surface is glass. Element 2: wherein the surface is black glass. Element 3: wherein preparing the sample further comprises wrapping the sample around a solid support, to provide a wrapped support, and wherein depositing lint from the sample onto the surface further comprises placing the wrapped support on the surface and moving the sample using a plowing motion in which the wrapped support is tilted forward, whereby a leading edge of the wrapped support makes substantially full contact with the surface, and a trailing edge of the wrapped support is lifted a distance off the surface. Element 4: wherein the distance is about ⅛ inch. Element 5: wherein the wrapped support is tilted forward at an angle of from about 5 to about 10 degrees from horizontal. Element 6: wherein the surface is substantially rectangular, having a long dimension and a short dimension. Element 7: wherein the solid support is substantially rectangular, having a long dimension and a short dimension, and wherein wrapping the sample around the solid support further comprises placing the solid support on the sample on a side of the sample opposite a side of the sample to contact the surface during lint deposition and wrapping the sample around the solid support, with a machine direction of the sample parallel to the short dimension of the solid support. Element 8: further comprising securing the sample to the solid support. Element 9: wherein placing the wrapped support on the surface provides an area of sample that contacts the surface during moving that is in the range of from about 8 to about 55 square inches. Element 10: wherein moving the sample on the support in a specific pattern comprising a plurality of directional changes further comprises moving the wrapped support back and forth along the long dimension of the surface, with the short dimension of the solid support parallel to the long dimension of the surface during the moving. Element 11: wherein moving the wrapped support back and forth along the long dimension of the surface further comprises positioning the wrapped support at a first position along the long dimension of the surface, moving the wrapped support in a plowing motion past a midway point along the long dimension to a second position along the long dimension of the surface, changing direction and moving the wrapped support in a plowing motion past the midway point along the long dimension to a third position along the long dimension of the surface, wherein the third position is closer to the midway point than the first position, wherein parallel alignment of the short dimension of the wrapped support with the long dimension of the surface is maintained during the moving, wherein movement of the wrapped support in a direction parallel to the short dimension of the surface is minimized, and wherein positioning of the wrapped support at a position along the long dimension of the surface comprises aligning the leading edge thereof with that position. Element 12: further comprising changing direction and moving the wrapped support in a plowing motion past the midway point along the long dimension to a subsequent position along the long dimension of the surface, wherein the subsequent position is closer to the midway point than the previous position on that side of the midway point. Element 13: further comprising changing direction and moving the wrapped support in a plowing motion past the midway point along the long dimension to a fourth position along the long dimension of the surface, wherein the fourth position is closer to the midway point than the second position; changing direction and moving the wrapped support in a plowing motion past the midway point along the long dimension to a fifth position along the long dimension of the surface, wherein the fifth position is closer to the midway point than the third position; changing direction and moving the wrapped support in a plowing motion past the midway point along the long dimension to a sixth position along the long dimension of the surface, wherein the sixth position is closer to the midway point than the fourth position; changing direction and moving the wrapped support in a plowing motion past the midway point along the long dimension to a seventh position along the long dimension of the surface, wherein the seventh position is closer to the midway point than the fifth position; and changing direction and moving the wrapped support in a plowing motion past the midway point along the long dimension to an eighth position along the long dimension of the surface, wherein the eighth position is closer to the midway point than the sixth position. Element 14: wherein the first and third positions are from about 5-10 inches from the midway point along the long dimension of the surface, the third and fourth positions are 1-2 inches closer to the midway point along the long dimension than the first and second positions, respectively, the fifth and sixth positions are 1-2 inches closer to the midway point along the long dimension than the third and fourth positions, respectively, and the seventh and eighth positions are 0.5-1.5 inches closer to the midway point along the long dimension than the fifth and sixth positions, respectively. Element 15: wherein the first and third positions are about seven inches from the midway point along the long dimension of the surface, the third and fourth positions are about 1.5 inches closer to the midway point along the long dimension than the first and second positions, respectively, the fifth and sixth positions are about 1.5 inches closer to the midway point along the long dimension than the third and fourth positions, respectively, and the seventh and eighth positions are about 1 inch closer to the midway point along the long dimension than the fifth and sixth positions, respectively. Element 16: wherein placing the wrapped support on the surface and moving the sample using a plowing motion begins by spraying the surface with an amount of glass cleaner prior to placing the wrapped support on the sprayed surface. Element 17: wherein the amount of glass cleaner comprises about 3 grams. Element 18: wherein spraying the glass surface with glass cleaner comprises wetting substantially the entire width of the surface near a midway point along the long dimension thereof, with the extent of the concentrated spray falling within about the center two thirds of the surface in the long dimension. Element 19: wherein placing the wrapped support on the sprayed surface comprises placing the wrapped support on the sprayed surface with a midway point along a short dimension thereof aligned with about the midway point of the surface in the long dimension. Element 20: further comprising, subsequent to placing the wrapped support on the sprayed surface, moving the wrapped support in a plowing motion to a first of two short sides along the short dimension of the surface, changing direction and moving the wrapped support in a plowing direction to a second of the two short sides of the surface, changing direction and moving the wrapped support in a plowing direction to the first of the two short sides of the surface, and changing direction and moving the wrapped support in a plowing direction back to the second of the two short sides of the surface. Element 21: wherein preparing the sample further comprises cutting the sample from a roll of paper towels. Element 22: wherein cutting the sample further comprises cutting the sample in the machine direction, avoiding any perforations. Element 23: wherein cutting the sample further comprises cutting the sample from a full sheet roll of paper towels, about ⅛ inch to the left of perforations thereof, or cutting the sample from a select-a-size roll of paper towels such that perforations thereof are positioned a maximum possible distance from a center of the sample in the machine direction. Element 24: wherein cutting the sample is performed with the side of the sample to be analyzed facing up. Element 25: wherein cutting the sample is performed just prior to depositing lint from the sample on the surface. Element 26: wherein preparing the sample further comprises conditioning the sample. Element 27: wherein conditioning the sample further comprises allowing the sample, the paper towel from which the sample is taken, a roll of paper towels from which is taken the paper towel from which the sample is taken, or a combination thereof, to acclimate in an area having a temperature of 72 degrees and a relative humidity of 50%. Element 28: wherein depositing lint from the sample onto the surface terminates by moving the wrapped support in a plowing motion to a position in which a midway point along a short dimension of the support is aligned with a midway point along a long dimension of the surface, and raising the wrapped support off the surface. Element 29: wherein collecting the lint deposited on the surface further comprises, substantially immediately upon depositing lint from the sample onto the surface, washing the deposited lint from the surface into a tared, cleaned, empty vessel. Element 30: wherein washing the deposited lint from the surface further comprises placing the surface in a raised support stand above a funnel, wherein the funnel is centered above the tared, cleaned, empty vessel. Element 31: wherein placing the surface in a raised support stand further comprises tipping the long dimension of the support to an angle from vertical, with a corner of the surface being the lowest point of the supported surface and pointing into the funnel. Element 32: wherein washing further comprises spraying the surface on which the lint has been deposited with rinse water via a water sprayer. Element 33: wherein washing with the water sprayer further comprises rinsing a 1-3 inch perimeter along two bottommost edges of the surface, such that the sprayed rinse water flows into the vessel. Element 34: wherein washing with the water sprayer further comprises wetting the innermost portions of the surface from a top to a bottom thereof, until substantially the entirety of the surface is wet. Element 35: wherein washing with the water sprayer further comprises rinsing two uppermost edges of the surface inward, and rinsing in a back and forth motion across the entire width of the surface, spraying across and down until there is a desired surface wash volume of rinse water in the vessel. Element 36: wherein the desired surface wash volume comprises about 180 grams of water. Element 37: wherein the rinse water is substantially lint-free prior to being sprayed. Element 38: wherein the water comprises de-ionized water, distilled water, or a combination thereof. Element 39: further comprising rinsing the funnel with rinse water, until there is a desired total wash volume of rinse water in the vessel. Element 40: wherein the total wash volume of rinse water is about 200 (±0.5) grams. Element 41: wherein the water sprayer provides water at a pressure in the range of from about 0.5 psi to about 10 psi, a flow rate in the range of from about 0.5 mL/s to about 5 mL/s, in substantially a single jet of water, or a combination thereof. Element 42: wherein determining the amount of collected lint further comprises measuring the number, the average length, and the average width of the fibers in the collected lint. Element 43: wherein determining the amount of collected lint comprises calculating the total fiber area (mm$^2$) of deposited lint from the sample, by multiplying the average fiber length (mm) by the average fiber width (mm) and the fiber count. Element 44: wherein determining the amount of collected lint further comprises measuring the number, the average length, and the average width of the fibers in an amount of collected lint in a blank, wherein the blank is obtained by collecting lint on the surface without the lint depositing step, calculating the total fiber area (mm$^2$) of deposited lint from the blank, by multiplying the average fiber length (mm) by the average fiber width (mm) and the fiber count, and subtracting the total fiber area of the blank from the total fiber area of deposited lint from the sample to obtain the amount of collected lint. Element 45: further comprising cleaning the surface prior to depositing the lint thereupon. Element 46: wherein cleaning the surface further comprises spraying the entire surface with glass cleaner, using a substantially lint-free squeegee to push the glass cleaner off one of two short sides of the surface, and using a substantially lint-free sponge to wipe the edges of the surface substantially free of lint. Element 47: wherein the paper towel is a retail paper towel. Element 48: wherein the specific pattern comprises a plurality of directional changes. Element 49: wherein washing further comprises spraying the surface on which the lint has been deposited with water via a spray gun. Element 50: wherein the spray gun provides water at a pressure in the range of from about 0.5 psi to about 10 psi, a flow rate in the range of from about 0.5 mL/s to about 5 mL/s, in substantially a single jet of water, or a combination thereof. Element 51: wherein the method is manual or automated.

While preferred embodiments of the invention have been shown and described, modifications thereof can be made by one skilled in the art without departing from the teachings of this disclosure. The embodiments described herein are exemplary only, and are not intended to be limiting. Many variations and modifications of the invention disclosed herein are possible and are within the scope of the invention.

Numerous other modifications, equivalents, and alternatives, will become apparent to those skilled in the art once the above disclosure is fully appreciated. It is intended that the following claims be interpreted to embrace all such modifications, equivalents, and alternatives where applicable. Accordingly, the scope of protection is not limited by the description set out above but is only limited by the claims which follow, that scope including all equivalents of the subject matter of the claims. Each and every claim is incorporated into the specification as an embodiment of the present invention. Thus, the claims are a further description and are an addition to the detailed description of the present invention. The disclosures of all patents, patent applications, and publications cited herein are hereby incorporated by reference, to the extent that they provide exemplary, procedural or other details supplementary to those set forth herein.

What is claimed is:

1. A method for quantitating the amount of lint shed from a paper towel, the method comprising:

preparing a sample of paper towel to be analyzed, wherein preparing the sample comprises wrapping the sample around a solid support, to provide a wrapped support;

depositing lint from the sample onto a surface, which has been cleaned, by moving the sample thereupon in a specific pattern;

collecting the lint deposited on the surface; and determining the amount of collected lint, wherein the surface is substantially rectangular, having a long dimension and a short dimension, wherein the solid support is substantially rectangular, having a long dimension and a short dimension, and wherein wrapping the sample around the solid support further comprises placing the solid support on the sample on a side of the sample opposite a side of the sample to contact the surface during lint deposition and wrapping the sample around the solid support, with a machine direction of the sample parallel to the short dimension of the solid support.

2. The method of claim 1, wherein the specific pattern comprises a plurality of directional changes.

3. The method of claim 1, wherein the method is manual.

4. The method of claim 1, wherein the method is automated.

5. The method of claim 1, wherein collecting the lint deposited on the surface comprises, substantially immediately upon depositing lint from the sample onto the surface, washing the deposited lint from the surface into a tared, cleaned, empty vessel.

6. The method of claim 5, wherein washing further comprises spraying the surface on which the lint has been deposited with water via a spray gun, and wherein the spray gun provides water at a pressure in the range of from about 0.5 psi to about 10 psi, a flow rate in the range of from about 0.5 mL/s to about 5 mL/s, in substantially a single jet of water, or a combination thereof.

7. The method of claim 6, wherein determining the amount of collected lint further comprises measuring the number, the average length, and the average width of the fibers in the collected lint, and calculating the total fiber area ($mm^2$) of deposited lint from the sample by multiplying the average fiber length (mm) by the average fiber width (mm) and the number of the fibers.

8. The method of claim 7, wherein determining the amount of collected lint further comprises measuring the number, the average length, and the average width of the fibers in an amount of collected lint in a blank, wherein the blank is obtained by collecting lint on the surface without the lint depositing step, calculating the total fiber area ($mm^2$) of deposited lint from the blank, by multiplying the average fiber length (mm) by the average fiber width (mm) and the number of the fibers, and subtracting the total fiber area of the blank from the total fiber area of deposited lint from the sample to obtain the amount of collected lint.

9. The method of claim 1, wherein determining the amount of collected lint further comprises measuring the number, the average length, and the average width of the fibers in the collected lint, and calculating the total fiber area ($mm^2$) of deposited lint from the sample by multiplying the average fiber length (mm) by the average fiber width (mm) and the number of the fibers.

10. The method of claim 9, wherein determining the amount of collected lint further comprises measuring the number, the average length, and the average width of the fibers in an amount of collected lint in a blank, wherein the blank is obtained by collecting lint on the surface without the lint depositing step, calculating the total fiber area ($mm^2$) of deposited lint from the blank, by multiplying the average fiber length (mm) by the average fiber width (mm) and the number of the fibers, and subtracting the total fiber area of the blank from the total fiber area of deposited lint from the sample to obtain the amount of collected lint.

11. A method for quantitating the amount of lint shed from a paper towel, the method comprising:

preparing a sample of paper towel to be analyzed, wherein preparing the sample comprises wrapping the sample around a solid support, to provide a wrapped support, wherein wrapping the sample around the solid support further comprises placing the solid support on the sample on a side of the sample opposite a side of the sample to contact the surface during lint deposition and wrapping the sample around the solid support;

depositing lint from the sample onto a surface, which has been cleaned, by moving the sample thereupon in a specific pattern comprising a plurality of directional changes;

collecting the lint deposited on the surface; and determining the amount of collected lint.

12. The method of claim 11, wherein the surface is substantially rectangular, having a long dimension and a short dimension, wherein the solid support is substantially rectangular, having a long dimension and a short dimension.

13. The method of claim 12, wherein wrapping the sample around the solid support comprises wrapping the sample around the solid support with a machine direction of the sample parallel to the short dimension of the solid support.

14. The method of claim 11, wherein the method is manual.

15. The method of claim 11, wherein the method is automated.

16. The method of claim 11, wherein collecting the lint deposited on the surface comprises, substantially immediately upon depositing lint from the sample onto the surface, washing the deposited lint from the surface into a tared, cleaned, empty vessel.

17. The method of claim 16, wherein washing further comprises spraying the surface on which the lint has been deposited with water via a spray gun, and wherein the spray gun provides water at a pressure in the range of from about 0.5 psi to about 10 psi, a flow rate in the range of from about 0.5 mL/s to about 5 mL/s, in substantially a single jet of water, or a combination thereof.

18. The method of claim 17, wherein determining the amount of collected lint further comprises measuring the number, the average length, and the average width of the fibers in the collected lint, and calculating the total fiber area ($mm^2$) of deposited lint from the sample by multiplying the average fiber length (mm) by the average fiber width (mm) and the number of the fibers.

19. The method of claim 18, wherein determining the amount of collected lint further comprises measuring the number, the average length, and the average width of the fibers in an amount of collected lint in a blank, wherein the blank is obtained by collecting lint on the surface without the lint depositing step, calculating the total fiber area ($mm^2$) of deposited lint from the blank, by multiplying the average fiber length (mm) by the average fiber width (mm) and the number of the fibers, and subtracting the total fiber area of the blank from the total fiber area of deposited lint from the sample to obtain the amount of collected lint.

20. The method of claim 11, wherein determining the amount of collected lint further comprises measuring the number, the average length, and the average width of the fibers in the collected lint, and calculating the total fiber area (mm²) of deposited lint from the sample by multiplying the average fiber length (mm) by the average fiber width (mm) and the number of the fibers.

21. The method of claim 20, wherein determining the amount of collected lint further comprises measuring the number, the average length, and the average width of the fibers in an amount of collected lint in a blank, wherein the blank is obtained by collecting lint on the surface without the lint depositing step, calculating the total fiber area (mm²) of deposited lint from the blank, by multiplying the average fiber length (mm) by the average fiber width (mm) and the number of the fibers, and subtracting the total fiber area of the blank from the total fiber area of deposited lint from the sample to obtain the amount of collected lint.

* * * * *